United States Patent [19]

Tracy et al.

[11] 4,313,764
[45] Feb. 2, 1982

[54] ISOCYANATE POLYOXYALKYLENES

[75] Inventors: David J. Tracy, Lincoln Park; Lindley S. Wood, Montclair; Paritosh M. Chakrabarti, Wayne, all of N.J.

[73] Assignee: GAF Corporation, New York, N.Y.

[21] Appl. No.: 174,047

[22] Filed: Jul. 31, 1980

[51] Int. Cl.$^3$ .................. C08L 1/12; C08L 33/20; C08L 77/06; D06M 13/42

[52] U.S. Cl. .................. 106/188; 260/453 AL; 525/123; 525/424; 525/440; 8/115.5; 8/115.7; 8/129; 8/181; 106/196

[58] Field of Search ............... 260/453 AL; 424/298; 525/123, 424, 440; 8/181, 115.5, 115.7, 129; 106/196, 188

[56] References Cited

U.S. PATENT DOCUMENTS

| | | | |
|---|---|---|---|
| 3,267,122 | 8/1966 | Lehmann et al. | 260/453 AL |
| 3,370,077 | 2/1968 | Hartzell | 260/453 AL |
| 3,631,199 | 12/1971 | Smith et al. | 260/453 AL |
| 4,089,649 | 5/1978 | Mares et al. | 8/115.5 |
| 4,148,819 | 4/1979 | Watts, Jr. et al. | 260/453 AL |

*Primary Examiner*—Dolph H. Torrence
*Attorney, Agent, or Firm*—James Magee, Jr.; Marilyn J. Maue

[57] ABSTRACT

The isocyanate polyoxyalkylenes having the formula:

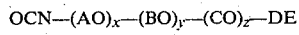

$$OCN-(AO)_x-(BO)_y-(CO)_z-DE \qquad I.$$

wherein E is —NCO or an amino group; A, C and D represent lower alkylene of 2 to 4 carbon atoms; B is alkylene of 2 to 8 carbon atoms; y and z are each integers having a value of 0 to 50 and x is an integer having a value of from 2 to 50, and intermixtures of said polyoxyalkylenes.

The above compounds display a wide variety of uses, namely for the control of fungi and bacteria or for the prevention of such infestation. They are also useful dielectric constant depressors for polymeric substances, e.g. polyvinylchloride, polyvinylidene halides, etc., extenders for solids in latices and anti-static agents.

1 Claim, No Drawings

ISOCYANATE POLYOXYALKYLENES

The products of the present invention are utilized as fungicides for paints and varnishes and as disinfectant cleaners for commercial, e.g. hospital use. Since the present products increase the water solubility of hydrophobic substances, they find application as emulsifiers for water insoluble monomers and modifiers for such polymers as nylons to render them more hydrophilic and other polymers such as acrylonitrile/vinylchloride copolymers (Dynel); cellulose triacetate (Arnel); terephthalic acid/ethylene glycol copolymers, e.g. Dacron, polyacrylonitrile, e.g. Orlon, polyamine/carboxylic acid condensation products, e.g. Nylons; polyethylene; polypropylene and other hydrophobic polyesters, polyamides, poly-acrylonitriles and polyalkylenes as well as their mixtures and/or blends with hydrophilic materials, such as cotton, wool and rayon. The present products are also antistatic agent for the above polymer fibers and impart increased dye penetration in the dyeing or printing of these fibers on fabrics. In general the present products increase the hydrophilicity of synthetic fibers, thereby providing for the development of more washable fabrics. While such synthetic fibers and materials have many advantageous properties, they have comparatively low capacity to retain moisture thus, accumulating electrostatic charges when subjected to normal friction as encountered in fabric processing or in wearing garments made of such fibers. The charged fibers also have the undesirable tendency to attract lint and soil and to give off spark discharges which, under certain circumstances, may constitute a serious hazard.

Accordingly, it is an object of this invention to overcome the above disadvantages and to provide economical isocyanate containing polyoxyalkylenes having a wide variety of uses.

Another object of this invention is to provide improved antistatic agents suitable for increasing the electrical conductivity of hydrophobic fabrics and formed plastics while exhibiting excellent high temperature stability and resistance to yellowing.

Still another object of the invention is to provide economical and efficient wetting agents and emulsifiers.

Another object is to provide oxidation inhibiting dispersants for dyes, pigments and paints.

Another object is to provide a novel group of fungicides for commercial use.

Still another object is to provide chemically inert extenders for solids in latex.

These and other objects and advantages of the present invention will become apparent from the following description and disclosure.

According to this invention, there is provided new and useful compounds which are isocyanate polyalkylenes having the formula:

wherein E is —W or an amino group; W is an isocyanate radical, i.e. O=C=N—; A, C and D represent lower alkylene of 2 to 4 carbon atoms; B is alkylene of 2 to 8 carbon atoms; y and z are each integers having a value of 0 to 50, and x is an integer having a value from 2 to 50, intermixtures of said polyoxyalkylenes. Of these compounds, those wherein x, y and z, taken together, average 7 to 60, A, C and D are the same and are ethylene or isopropylene, are preferred. Of this preferred group, those most desirable are the compounds wherein y and z are 0; x is an integer between 7 and 25 and E is —W. However, it is to be understood that the value of x, y and z, as well as the radicals A, B, C and D in the above compounds and their mixtures, can be varied considerably in accordance with the needs of the particular application in which the product is to be employed.

Examples of isocyanate polyoxyalkylenes within the preferred group of compounds include the compounds having the subgeneric formulae:

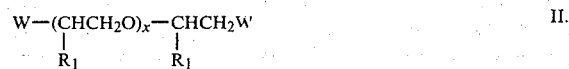

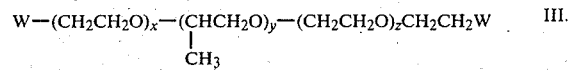

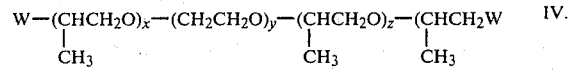

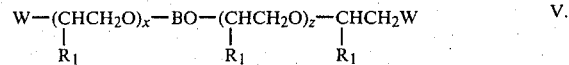

where, in each of formulae II and V, $R_1$ is hydrogen or methyl; W is —NCO; and wherein B, in formula V is alkyl of 4 to 8 carbon atoms; x in formula II is an integer having a value of 2 to 25; x and z in formulae III, IV and V are integers having a value of 2 to 20 and y in formulae III and IV is an integer having a value of 1 to 20.

Although it is to be understood that individual compounds within the scope of Formula I can be isolated by extraction, gel permation chromatography, or any other convenient method, the products of the present invention are usually employed as mixtures wherein at least x, or x and y, have different values within the above ranges. Such mixtures are also contemplated wherein A, B and/or C represent different alkylene groups, as well. These mixtures have significantly higher boiling points and are more compatible with hydrocarbon chemicals than the individual polymers.

In general, the compounds of the present invention are economical to prepare since most are derived from readily available starting materials. The preparation of the present compounds involves the reaction of said diamino derivative of said polyoxyalkylene, i.e. $H_2N$—$(AO)_x$—$(BO)_y$—$(CO)_z$—$DNH_2$ with a stoichiometric amount of phosgene.

The preferred ratio of polyoxyalkylene diamine to coreactant is as close to 1:1 stoichiometry as is convenient to maintain, depending on the product desired. Generally, when a monoamine product is desired as the product of the process, a mole ratio of between about 1.4:1 and about 1:1.5 is satisfactory. However, when it is desirable to replace both terminal amino groups with the isocyanate radical, a mole ratio of between about 1:2 and about 1:5 can be employed. It should be understood that, although a higher excess of phosgene reactant can be employed if desired, there is no benefit to be derived therefrom.

The present reaction is carried out under anhydrous conditions in the presence of an organic solvent. Suitable solvents, when employed, are those inert organic solvents having a boiling point above the reaction temperature. Typical solvents of this type include amyl benzene toluene, xylene, naphthalene, pyridone, pyrrolidone, cyclohexanol, octanol, chlorobenzene, cycloheptane, dimethylformamide, N-methylpyrrolidone, dimethylsulfoxide, hexamethyl-phosphoramide and alkanes having from 9 to 12 carbon atoms including cyclic and branched chain hydrocarbons. When employed, the concentration of solvent in the system may vary between about 5 and about 50 weight %, preferably not more than 30 weight %, based on the reactants in the reaction zone.

The present reaction is effected at a temperature of between about 70° C. and about 225° C., under from about 10 to about 50 psi, and is completed in a period of from about 4 to about 20 hours; preferably the reaction is carried out between about 90° C. and about 190° C., under from atmospheric to about 20 psi, and is completed within 8 to about 15 hours, depending upon the degree of conversion desired and the molecular weight of the polymeric reactant. Although the reaction can be carried out in an open or a closed system, closed system operation provides better temperature control and a more accurate determination of the percent conversion. The di-isocyanate products of the present process can be directly obtained in a purity of up to 98%, when a solvent is omitted. However, the solvents, when used, can be easily removed by distillation or any other convenient method.

The amines of this invention can be prepared in a conventional manner by ammoniating the corresponding halide or by catalytic reaction of the corresponding glycol with ammonia and hydrogen at between about 150° C. and 290° C. under from 5000 psig to about 500 psig pressure, employing stoichiometric amounts of reactants.

The amines of this invention are those having the general formula $$H_2N-(AO)_x-(BO)_y-(CO)_z-DNH_2$$

wherein A, C and D are lower alkylene of 2 to 4 carbon atoms; B is alkylene of 2 to 8 carbon atoms; y and z have a value of 0 to 50 and x has a value of from 2 to 50.

Glycols useful for making the present amines are commercially marketed by Wyandotte Chemicals Corporation under the tradename Polyol and by GAF Corporation under the tradename PEG polymer.

Polyols supplied by Wyandotte Chemicals Corp. of which the Polyols P104, F108, L43, 25R2, P85 and F127 are among those most desirable for the polymeric moiety of the present polymeric diamines, other suitable types are shown on accompanying Table I.

TABLE I

| Form* | Pluronic Grade | Average Molecular Weight | Flash Point (COC) °F. | Refractive Index 25° C. |
|---|---|---|---|---|
| L | 10R5 | 1970 | 450 | 1.4587 |
| F | 10R8 | 5000 | 450 | — |
| L | 17R1 | 1950 | 450 | 1.4516 |
| L | 17R2 | 2100 | 450 | 1.4535 |
| L | 17R4 | 2700 | 450 | 1.4572 |
| F | 17R8 | 7500 | 450 | — |
| L | 25R1 | 2800 | 450 | 1.4521 |
| L | 25R4 | 3800 | 450 | 1.4574 |
| P | 25R8 | 4500 | 450 | — |
| F | 25R8 | 9000 | 450 | — |
| L | 31R1 | 3200 | 450 | 1.4522 |
| L | 31R2 | 3400 | 450 | 1.4542 |
| P | 31R4 | 4300 | — | — |
| | L31 | 1100 | 37 | — |
| | L35 | 1900 | 77 | — |
| | F38 | 5000 | 100 | 45 |
| | L42 | 1630 | 37 | — |
| | L43 | 1850 | 42 | — |
| | L44 | 2200 | 65 | — |

TABLE I-continued

| Form* | Pluronic Grade | Average Molecular Weight | Flash Point (COC) °F. | Refractive Index 25° C. |
|---|---|---|---|---|
| | L61 | 2000 | 24 | — |
| | L62 | 2500 | 32 | — |
| | L62LF | 2450 | 28 | — |
| | L62D | 2750 | 35 | — |
| | L63 | 2650 | 34 | — |
| | L64 | 2900 | 58 | — |
| | P65 | 3500 | 82 | 29.5 |
| | F68 | 8350 | 100 | 50 |
| | F68LF | 7700 | 32 | 47 |
| | L72 | 2850 | 25 | — |
| | P75 | 4150 | 82 | 34 |
| | F77 | 6500 | 100 | 48 |
| | L81 | 2750 | 20 | — |
| | P84 | 4200 | 74 | 34 |
| | P85 | 4600 | 85 | 40 |
| | P87 | 7850 | 100 | 49 |
| | F88 | 10,800 | 100 | 55 |
| | F92 | 3500 | 26 | — |
| | F94 | 4600 | 76 | 38 |
| | F98 | 13,500 | 100 | 56 |
| | L101 | 3800 | 15 | — |
| | P103 | 4900 | 86 | 30 |
| | P104 | 5800 | 81 | 37.5 |
| | P105 | 6350 | 91 | 42 |
| | F108 | 15,500 | 100 | 57 |
| | L121 | 4500 | 14 | — |
| | L122 | 4900 | 19 | — |
| | F123 | 5650 | 90 | — |
| | P127 | 11,500 | 100 | 56 |

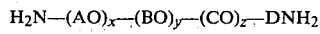
L-Liquid
P-Paste
F-Flakeable Solid

As stated above, the isocyanate capped polymeric products of the present invention are useful in synthetic textile and polymer modification and as additives in many fields of application, as they are much more stable than the corresponding cyanates which readily trimerize with loss of activity. Generally, their use as additives to formulations, such as paint vehicles, polymerization media, dye baths, commercial cleansers, oil based lubricants, etc. involves utilization of the present compounds in a wide range of concentrations, e.g. from as little as about 0.05% to about 20% by weight, preferably from about 0.1% to about 10% by weight based on the formulation.

For fungicidal use, the present products are employed in concentrations of between about 25 to about 10,000 ppm in a suitable inert carrier or in a formulation containing other agriculturally active ingredients which do not materially affect the activity of the present polymeric isocyanates.

All of the products of the present invention are antistatic agents which can be impregnated into hydrophobic fabrics by padding about 1.5 to about 20 parts per 100 parts of fabric followed by drying and curing. As an antistatic agent, the present product is usually employed in aqueous solution in a concentration of between about 0.05 and about 3%. The material so finished shows a marked decrease in electrical resistivity, such that the electrostatic conductivity of a specific area of fabric is increased to $10^{-14}$ or a higher reciprocal ohm.

Having generally described the invention, reference is now had to the accompanying examples which illustrate preferred embodiments but which are not to be construed as limiting to the scope of the invention as set forth above and as defined in the accompanying claims. All amounts and proportions recited in the following examples are by weight, unless otherwise indicated.

EXAMPLE I

A. Into a glass round bottom flask equipped with stirrer, condenser and thermometer is added 116.8 grams of polyoxyalkylene diamine having the formula:

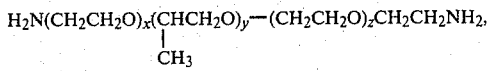
$$H_2N(CH_2CH_2O)_x(CHCH_2O)_y-(CH_2CH_2O)_zCH_2CH_2NH_2,$$
$$|$$
$$CH_3$$

wherein x and y are 2 and z is 1, and 200 ml. of amylbenzene. Hydrogen chloride is bubbled in until no more uptake is observed (saturated solution). The mixture is heated to boiling (180°–185°) and phosgene is bubbled in until a clear solution is obtained. The solvent is stripped leaving a dark red very viscous liquid of the corresponding diisocyanate (108 grams)

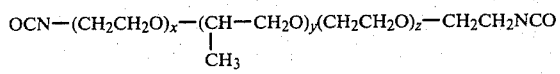
$$OCN-(CH_2CH_2O)_x-(CH-CH_2O)_y(CH_2CH_2O)_z-CH_2CH_2NCO$$
$$|$$
$$CH_3$$

in 80% yield and 90% purity.

B. The above Example is repeated except that in the polyoxalkylenediamine, x, y and z average 18 and y is a mixture of 4 to 6 units. About 500 ml. of amylbenzene solvent is employed and the hydrogen chloride saturated solution is boiled while bubbling through stoichiometric excess of phosgene whereupon the solution clears. The corresponding isocyanate product is obtained in 85% yield and comprises a mixture of 4:1 diisocyanate and monoisocyanate having the formulae:

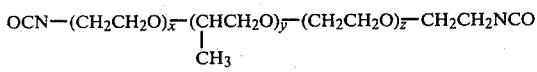
$$OCN-(CH_2CH_2O)_{\overline{x}}-(CHCH_2O)_{\overline{y}}-(CH_2CH_2O)_{\overline{z}}-CH_2CH_2NCO$$
$$|$$
$$CH_3$$
and
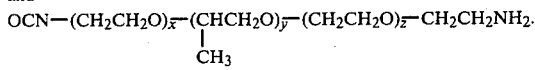
$$OCN-(CH_2CH_2O)_{\overline{x}}-(CHCH_2O)_{\overline{y}}-(CH_2CH_2O)_{\overline{z}}-CH_2CH_2NH_2.$$
$$|$$
$$CH_3$$

C. The reaction of 1B is repeated except that the mole ratio of the polyoxalkylenediamine:phosgene is maintained at a ratio of about 1:0.5–0.7. The product obtained contains about 40% of the monoisocyanate derivative.

It is to be understood that other isocyanate products made from other polymeric mixtures wherein the average of x, y and z is, for example 10, 12, 16, 24 or higher and wherein the polymeric product contains at least two different monomeric units, such as for example wherein A, C and D are ethylene or isopropylene and B is butylene pentylene, hexylene, heptylene or octylene, and many other combinations which are apparent from the foregoing description and disclosure, can be substituted in Example 1 to impart effective antistatic properties.

EXAMPLE 2

The product of Example 1A is dissolved in methylene chloride to provide two 2% solutions. A 1.5×11.5 inch strip of Dacron 56 Taffeta is immersed in each of the solutions for approximately 10 minutes. The impregnated strips are then removed and air dried without curing and tested for electrostatic build-up. The impregnated strips are stroked 50 times against a polyvinylchloride fabric surface and then placed on top of an ashtray containing cigarette ashes. There is no ash pick-up on the strip which indicates complete discharge of static electricity.

The product of Example 1A is not merely formed as a coating film on the fabric but actually penetrates into the intersticies of the weave and has affinity for the fabric such that the antistatic property has a more lasting affect and the fabric strip so treated can withstand several launderings without lowering the specific area conductivity below $10^{-14}$ reciprocal ohm as determined by measurement, with a wheatstone bridge, of the electrical resistance of the strip and converting to the reciprocal.

EXAMPLE 3

Seven rose bushes, five cucumber vines and five peach trees all infected with mildew are sprayed to run off with an aqueous solution containing 500 ppm of the isocyanate product of Example 1B. One species of each plant are infected but left untreated as a control. After 6 days leaves of each untreated plant are 100% infected with powdery mildew; whereas all treated plants show 0% infection. When the experiment is repeated and the dosage level of the isocyanate product is reduced to 300 ppm in aqueous solution, only 1% or 2% infection remains.

It is to be understood that other isocyanate compounds of this invention possess similar fungicidal properties when used in the above dosages.

EXAMPLE 4

The products of Examples 1A–1C are separately added to one of two one quart cans of outdoor white latex paint to provide 2% mixtures therein and the mixtures stirred for two hours. The resulting paint mixtures are noticeably thickened and the paint of each quart shows improved resistance to mildew when compared with untreated paint after a period of 6 months in an atmosphere of 80–85% humidity.

It is to be understood that isocyanate products made from other polyoxyalkylene mixtures wherein the average of x, y and/or z is, for example 10, 12, 16, 24 or higher and wherein the polymeric diamide contains at least two different monomeric units, such as for example wherein A, C and D are ethylene and B is isopropylene or wherein A, C and D are isopropylene and B is ethylene or wherein Z is zero and A and D are isopropylene and B is ethylene or wherein z is zero and A and D are ethylene and B is isopropylene or wherein y and D are zero and x has a value of from 7 to 25 and A is either ethylene or propylene or any of the above mixtures for A and D or A, C and D where B is butylene, pentylene, hexylene, heptylene or octylene and many other combinations which are apparent from the foregoing description and disclosure, can be substituted in Examples 2 through 4 to give good results.

What we claim is:

1. The process of increasing the hydrophilicity of an hydrophobic polymeric material by incorporating in said material between about 0.01 and about 10 weight percent of an isocyanate of polyoxyalkylene product having the formula:

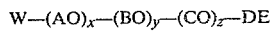
$$W-(AO)_x-(BO)_y-(CO)_z-DE$$

wherein E is amino or —W; W is an isocyanate radical; A, C and D represent lower alkylene of 2 to 4 carbon atoms; B is alkylene of 2 to 8 carbon atoms; y and z are each integers having a value of from 0 to 50; x is an integer having a value of from 2 to 50; and intermixtures of said isocyanate polyoxyalkylene compounds.

* * * * *